US007265153B2

(12) United States Patent
Faller et al.

(10) Patent No.: US 7,265,153 B2
(45) Date of Patent: Sep. 4, 2007

(54) COMPOSITIONS AND METHODS FOR THE TREATMENT OF CYSTIC FIBROSIS

(76) Inventors: Douglas V. Faller, 45 Beaver Rd., Weston, MA (US) 02193; Susan P. Perrine, 45 Beaver Rd., Weston, MA (US) 02193; George Stamatoyannopoulos, 702 35th Ave., Seattle, WA (US) 98122

( * ) Notice: Subject to any disclaimer, the term of this patent is extended or adjusted under 35 U.S.C. 154(b) by 0 days.

(21) Appl. No.: 10/185,745

(22) Filed: Jul. 1, 2002

(65) Prior Publication Data
US 2003/0018069 A1 Jan. 23, 2003

Related U.S. Application Data

(62) Division of application No. 09/248,260, filed on Feb. 11, 1999, now abandoned.

(60) Provisional application No. 60/074,304, filed on Feb. 11, 1998.

(51) Int. Cl.
*A61K 31/19* (2006.01)
(52) U.S. Cl. ..................................... 514/557
(58) Field of Classification Search ................ 514/557
See application file for complete search history.

(56) References Cited

U.S. PATENT DOCUMENTS

| 4,704,402 A | 11/1987 | Abraham et al. |
| 4,723,958 A | 2/1988 | Pope et al. |
| 4,747,825 A | 5/1988 | Linkie et al. |
| 4,958,592 A | 9/1990 | Anthony et al. |
| 4,965,251 A | 10/1990 | Stamatoyannopoulos |
| 5,100,647 A | 3/1992 | Agus et al. |
| 5,403,590 A | 4/1995 | Forse |
| 5,674,898 A | 10/1997 | Cheng et al. |
| 5,750,571 A | 5/1998 | Cheng et al. |
| 5,846,528 A | 12/1998 | Podsakoff et al. |
| 5,858,365 A | 1/1999 | Faller et al. |
| 5,939,456 A | 8/1999 | Perrine et al. |

FOREIGN PATENT DOCUMENTS

| WO | WO92/04913 | 4/1992 |
| WO | WO93/18761 | 9/1993 |
| WO | WO94/04671 | 3/1994 |
| WO | WO95/11699 | 5/1995 |
| WO | WO96/27369 | 9/1996 |
| WO | WO97/04761 | 2/1997 |
| WO | WO98/04290 | 2/1998 |
| WO | WO98/40078 | 9/1998 |
| WO | WO98/56370 | 12/1998 |

OTHER PUBLICATIONS

Rubenstein, et al.: "A pilot clinical trial of oral sodium 4-phenylbutyrate (Buphenyl) In DELTAF508-homozygous cystic fibrosis patients: Partial restoration of nasal epithelial CFTR function" American Journal of Respiratory and Critical Care Medicine, (Feb. 1998), vol. 157, No. 2 pp. 484-490.
Walsh, et al.: "Combination of Drug and Gene Delivery by Gelatin Nanospheres for the Treatment of Cystic Fibrosis" Proceedings of the International Symposium on Controlled Release of Bioactive Materials, U.S., Deerfield, IL, controlled Release Soc., vol. SYMP, 24, Jun. 15, 1997, pp. 75-76.
Rubenstein et al.: "In vitro pharmacologic restoration of CFTR-mediated chloride transport with sodium 4-phenylbutyrate in cystic fibrosis epithelial cells containing delta.F508-CFTR" Journal of Clinical Investigation, U.S., New York, NY, vol. 10, No. 100, Nov. 15, 1997, pp. 2457-2465.
Konstan, Michael et al.: "Effect of High-Dose Ibuprofen in Patients with Cystic Fibrosis", New England Journal of Medicine, (1995) vol. 332, No. 13, pp. 848-854.
Cheng, S.H. et al., Functional activation of the cystic fibrosis trafficking mutant $\Delta$F508-CFTR by expression, Am. J. Physiol., 268:L615-24 (1995).

*Primary Examiner*—Raymond J. Henley, III
(74) *Attorney, Agent, or Firm*—Nixon Peabody LLP

(57) ABSTRACT

The invention is directed to novel pharmaceutical compositions comprising chemicals agents that are useful in the treatment and prevention of cystic fibrosis and the prevention of signs and symptoms of this disease. These pharmaceutical compositions are surprisingly successful in the treatment disorders related to cystic fibrosis including disorders of blood production. Many of these compositions of the invention are even more effective when administered to a patient in pulses. Pulse therapy is not a form of discontinuous administration of the same amount of a composition over time, but comprises administration of the same dose of the composition at a reduced frequency or administration of reduced doses.

17 Claims, No Drawings

COMPOSITIONS AND METHODS FOR THE TREATMENT OF CYSTIC FIBROSIS

CROSS-REFERENCE TO RELATED APPLICATION

This Divisional Application claims the benefit under 35 U.S.C. §120 of U.S. Ser. No. 09/248,260, filed Feb. 11, 1999, now abandoned which claims the benefit under 35 U.S.C. § 119(e) of U.S. Provisional Application No. 60/074,304, filed Feb. 11, 1998.

FIELD OF THE INVENTION

The invention relates to pharmaceutically acceptable compositions for administration to humans to treat cystic fibrosis and also to methods for effectively utilizing these compositions.

BACKGROUND OF THE INVENTION

Cystic fibrosis (CF) is a systemic disorder that results when mutations in the cystic fibrosis transmembrane conductance regulator (CFTR), an apical membrane glycoprotein, lead to a reduction in apical membrane chloride transport. CFTR is a cAMP-dependent chloride channel that regulates fluid composition in the respiratory and gastrointestinal tracts. CF is a heritable disease that follows an autosomal recessive pattern of transmission. It is the most common invariably lethal genetic disease in the United States, with frequency among Caucasians being one in two thousand. One in twenty are carriers of the defective gene. CF is characterized by abnormal endocrine and exocrine gland function. In CF, unusually thick mucus leads chronic pulmonary disease and respiratory infections, insufficient pancreatic and digestive function, and abnormally concentrated sweat. Seventy percent of the mutant CFTR alleles in the Caucasian population result from deletion of phenylalanine at position 508 ($\Delta$F508-CFTR), the result of a three base pair deletion in the genetic code. Other mutations have also been described and many may exist. The $\Delta$F508-CFTR mutation results in a CFTR protein capable of conducting chloride, but absent from the plasma membrane because of aberrant intracellular processing. Under usual conditions (37° C.), the $\Delta$F508-CFTR protein is retained in the endoplasmic reticulum (ER), by prolonged association with the ER chaperones, including calnexin and hsp70. The retained CFTR protein is then targeted for degradation by the ubiquitin proteasome pathway. Over expression of $\Delta$F508-CFTR can result in $\Delta$F508-CFTR protein appearing at the cell surface, and this protein is functional once it reaches the cell surface. The $\Delta$F508 "trafficking" block is also reversible by incubation of cultured CF epithelial cells at reduced temperatures (25-27° C.). Lowered temperature results in the appearance of CFTR protein and channel activity at the cell surface, suggesting an intrinsic thermodynamic instability in $\Delta$F508-CFTR at 37° C. that leads to recognition of the mutant protein by the ER quality control mechanism, prevents further trafficking, and results in protein degradation. High concentrations of glycerol (1 M or 10%), a protein stabilizing agent or chemical chaperone, also appears to facilitate movement of $\Delta$F508-CFTR from the ER to the plasma membrane.

Some of the palliative treatments involve the administration of biologically active proteins or chemical compounds to decrease the viscosity of secretions, or to suppress chronic infections of the airways. These treatments have a number of limitations, and do not address the illness directly, but rather attempt to treat the symptoms. Some require continuous use at fairly high doses while others have short effective half-lives. Tolerance to the active ingredient often develops rendering the composition functionally useless. In addition to problems associated with tolerance, the substances themselves or their metabolic by-products or carriers can quickly reach toxic levels in the patient's system which impair kidney or liver function. Further, the chemical compounds themselves can be rapidly destroyed by catabolic enzymes, found in the cells and serum such as aminases, oxidases and hydrolases. Many of these enzymes are also found in hepatic cells, the principal sites for cleansing of the blood. Those able to survive cellular and hepatic catabolic processes are quickly eliminated from the patient's system by the kidneys. Consequently, in vivo retention times for active compounds are extremely short and the ability to achieve any sort of sustained biological effect becomes nearly impossible or, at least, impractical.

Gene therapy for cystic fibrosis has been attempted, but has not been successful to date for a number of reasons, including problems with delivery of the gene to airway cells, insufficient levels of gene expression, inadequate duration of gene expression, and toxicity of the gene therapy preparations.

A recent publication used 4-phenylbutyrate (4PBA) to enable a greater fraction of $\Delta$F508-CFTR to escape degradation and appear at the cell surface (Rubenstein, R. C., Egan, M. E., and Zeitlin, P. L. In vitro pharmacologic restoration of CFTR-mediated chloride transport with sodium 4-phenyl butyrate in cystic fibrosis epithelial cells containing delta-F508-CFTR. J. Clin. Invest. 100:2457-65, 1997). Briefly, primary cultures of nasal polyp epithelia from CF patients ($\Delta$F508 homozygous or heterozygous), or the CF bronchial epithelial cell line IB3-1 ($\Delta$F508/W1282X) were exposed to 4PBA for up to 7 days in culture. 4PBA treatment at concentrations of 0.1 and 2 mM resulted in the restoration of forskolin-activated chloride secretion. Protein kinase A-activated, linear, 10 pS chloride channels appeared at the plasma membrane of IB3-1 cells at the tested concentration of 2.5 mM 4PBA. Treatment of IB3-1 cells with 0.1-1 mM 4PBA and primary nasal epithelia with 5 mM 4PBA also resulted in the appearance of higher molecular mass forms of CFTR, consistent with addition and modification of oligosaccharides in the Golgi apparatus, as detected by immunoblotting of whole cell lysates with anti-CFTR antisera. Immunocytochemistry in CF epithelial cells treated with 4PBA was consistent with increasing amounts of $\Delta$F508-CFTR.

As 4PBA is an analogue of butyrate, a known transcriptional regulator of CFTR expression (Cheng, S. H., Fang, S. L., Zabner, J., Marshall, J., Piraino, S., Schiavi, S. C., Jefferson, D. M., Welsh, M. J., and Smith, A. E. Functional activation of the cystic fibrosis trafficking mutant $\Delta$F508-CFTR by expression. Am. J. Physiol. 268:L615-24, 1995), it was hypothesized that 4PBA might increase transcription of the $\Delta$F508-CFTR allele (Rubenstein et al.). If it were a transcriptional regulator, 4PBA might thereby increase levels of $\Delta$F508-CFTR protein, and by mass action, would force some $\Delta$F508-CFTR to bypass quality control in the ER. Such a mechanism would be consistent with the observations that butyrate itself can induce cAMP-responsive was indicated to be possibly clinically useful, works though a mechanism, which although unknown, is different from butyrate. Taken together, the use of butyrate, and the newer butyrate-derived compounds claimed, as CF therapeutics is contra-indicated according to these reports. Moreover, 4PBA has been used in a few CF patients clinically, but was not well tolerated due to large number of pills required (i.e. very short half-life), and other side effects and, in consideration, that study was terminated.

DESCRIPTION OF THE INVENTION

As embodied and broadly described herein, the present invention is directed to novel chemicals and novel pharmaceutical compositions comprising these and other chemicals that can be used in the treatment and prevention of diseases and disorders associated with cystic fibrosis. The invention is further directed to methods for the administration of these pharmaceutical compositions to patients for the treatment of cystic fibrosis and prevention of its signs and symptoms.

It has been discovered that a group of chemicals and pharmaceutical compositions containing one or more such chemicals are surprisingly successful in the treatment of cystic fibrosis and other disorders including, for example, disorders of blood production. Also surprisingly, it was discovered that many of these compositions are even more effective when administered to a patient in pulses. Pulse therapy is not a form of discontinuous administration of the same amount of a composition over time, but comprises administration of the same dose of the composition at a reduced frequency or administration of reduced doses.

According to these methods, cystic fibrosis and other disorders can be effectively treated and without unnecessary adverse side effects to the patient. Although most compositions are generally safe and non-toxic at therapeutic doses, pulsed administration further reduces risks associated with, for example, toxicity, allergic reactions, the build-up of toxic metabolites and inconveniences associated with conventional treatment. In addition, these chemical compositions, now useful at a substantially reduced dose and frequency, have a significantly reduced risk of complications such as, for example, induced tolerance. These compositions are not inactivated by cellular enzymes or cleared from cells and organs prior to having the desired effect. Further, long-term therapy, typically required for the amelioration of many blood disorders, can be successfully performed. Consequently, doses necessary for maintaining a constant effect for the patient are steady and material costs and inconveniences associated with administration are substantially reduced.

The mechanism of action of many of the chemical compounds or active ingredients of compositions for the treatment of cystic fibrosis involves effecting one or more of the processes of gene transcription, protein translation or processing or transport or stability, cell proliferation, cell recruitment, cell differentiation, or CFTR expression or activity. Gene expression can be increased or decreased by altering chromatin and/or nucleosome structure to render a genetic element more or less susceptible to transcription, by altering DNA structure, for example, by methylation of G residues, by affecting the activity of cell-specific transcription or translation factors such as activators or repressors, or by increasing the rate of transcription or translation. CFTR expression can be increased or decreased by affecting gene expression, peptide expression, CFTR assembly, CFTR glycosylation or transport through the Golgi apparatus or the stability of the CFTR molecule. Cell proliferation may be increased, for example, by stimulating stem cells, pulmonary or pancreatic or other secretory cell growth, or decreased, for example, by effecting a cell's period in or ability to transverse a stage (S, G2, G1, M) of the cell cycle. Cell recruitment may be promoted through the expression of specific cytokines such as cell surface receptors or secreted factors. CFTR function may be increased by promoting chloride transport or other activities of the protein.

Chemical agents that can be administered as pharmaceutical compositions include phenoxyacetic acid, methoxyacetic acid, butyric acid ethyl ester, cinnamic acid, hydrocinnamic acid, alpha-methyl cinnamic acid and alpha-methylhydrocinnamic acid (alpha-MHCA) which stimulate alterations in binding or removal of transcription factors from the proximal promoter region of certain genes or gene clusters and thereby increase suppressed gene expression, or serve a chaperones to facilitate processing, transport and the thermal or physical stability of mutated or normal CFTR proteins.

These compositions preferably increase the expression of CFTR, increase the expression of CFTR genes, increase the number of CFTR-expressing cells or increase the activity of CFTR. Preferably, compositions also increase CFTR expression or function greater than about 30%, more preferably greater than about 100%, and even more preferably greater than about 200%. CFTR intracellular and cell surface expression, gene expression and cell proliferation can be assayed by measuring fold increases in expressed amounts of specific mRNA, protein or numbers of CFTR-expressing cells in treated samples as compared to untreated controls. Utilizing this criteria, compositions preferably increase the amount of CFTR cell surface expression, the amount of CFTR gene expression, the number of CFTR-expressing cells by greater than or equal to about 1½-fold, preferably about two-fold and more preferably about four-fold. CFTR function can be measured by analysis of chloride ion transport/efflux (cAMP-stimulated or otherwise), patch clamping, sweat testing, or improvement in the symptoms of cystic fibrosis.

One embodiment of the invention is directed to pharmaceutical compositions comprising one or more novel chemical agents. Agents include chemicals of the structure $R_1$—$R_2$—$R_3$ or, preferably, $R_1$—C(O)—$R_2$—$R_3$ wherein $R_1$ is $CH_x$, CO, $nH_x$, $NH_x$, $OH_x$, $SH_x$, $COH_x$, $CONH_x$, COOH or $COSH_x$; $R_2$ is $CH_x$ or a branched or linear alkyl chain; $R_3$ is $CONH_x$, $COSH_x$, COOH, $COOR_4$, $COR_4$, CO or $OR_4$; $R_4$ is $CH_x$, CO, $H_x$, $NH_x$, $OH_x$, $SH_x$ or a branched or linear alkyl chain; phenyl-$R_5$—$R_6$—$R_7$ wherein phenyl is a six carbon benzyl ring or a hydrogenated, hydroxylated or halogenated six carbon ring; $R_5$ is $CH_x$, CO, $NH_x$, $OH_x$ or $SH_x$: $R_6$ is $CH_x$, CO, $H_x$, $NH_x$, $OH_x$, $SH_x$, or a branched or linear alkyl chain; $R_7$ is $CH_x$, $H_x$, $NH_x$, $OH_x$, $SH_x$, CO, $CONH_x$, COOH, $COSH_x$, $COOR_8$, $COR_8$ or $OR_8$; $R_8$ is $CH_x$, CO, $H_x$, $NH_x$, $OH_x$, $SH_x$ or a branched or linear aryl chain; and phenyl-$R_9$—$R_{10}$ wherein $R_9$ is $CH_x$, CO, $NH_x$, $OH_x$, $SH_x$, or a branched or linear aryl chain; $R_{10}$ is $CH_x$, CO, $H_x$, $NH_x$, $OH_x$, $SH_x$, $CONH_x$, COOH, $COSH_x$, $COOR_{11}$, $COR_{11}$, CO or $OR_{11}$; and $R_{11}$ is $CH_x$, CO, $H_x$, $NH_x$, $OH_x$, $SH_x$ or a branched or linear alkyl chain; wherein x is 0, 1, 2 or 3. Preferably, $R_4$ comprises between 1 to 8 carbon atoms and more preferably 1, 2, 3 or 4 carbon atoms. Preferably, $R_6$ comprises between 1 to 8 carbon atoms and more preferably 1, 2, 3 or 4 carbon atoms. Preferably, $R_8$ comprises between 1 to 8 carbon atoms and more preferably 1, 2, 3 or 4 carbon atoms.

Examples of chemical compounds of the structure $R_1$—$R_2$—$R_3$ or $R_1$—C(O)—$R_2$—$R_3$ include acids, amines, monoamides and diamides of butyric acid ($H_3C$—$CH_2$—$CH_2$—COOH), butyric acid ethyl ester ($CH_3CH_2CH_2COCH_2CH_3$) 4,4,4-tri fluorobutyric acid ($CF_3CH_2CH_2COOH$), 2,2-dimethyl butyric acid ($C_2H_5C(CH_3)_2CO_2H$), 2,2-diethyl butyric acid, 3,3-dimethyl butyric acid ($C_6H_{12}O_2$), 3,3-diethyl butyric acid, fumaric acid (HOOCCH=CHCOOH), fumaric acid monomethyl and monoethyl ester, fumaric acid monoamide ($C_4H_5O_2N$), fumaramide ($H_2NCOCHCHCONH_2$), succinic acid (HOOCCH$_2$CH$_2$COOH) (succinamic acid and succinamide), 2,3-dimethyl succinic acid and methoxy acetic acid ($CH_3CH_2OCH_3$).

Examples of chemical compounds of the structure phenyl-$R_5$—$R_6$—$R_7$ include acids, amines and amides of phenoxyacetic acid ($C_6H_5OCH_2COOH$; $C_6H_5$ $OCH_2COONH_3$), 2- and 3-thiophenoxy propionic acid ($C_6H_5SCH(CH_3)COOH$; $C_6H_5$ $SCH_2CH_2COOH$), 2- and 3-phenoxy propionic acid ($C_6H_5OCH(CH_3)COOH$; $C_6H_5OCH_2$ $CH_2COOH$), 2- and 3-phenyl propionic acid ($C_6H_5CH(CH_3)COOH$; $C_6H_5CH_2CH_2$ COOH), 4-chlorophenoxy-2-propionic acid ($ClC_6OCH_2CH_2CO_2H$), methoxy acetic acid ($H_3COCH_2CO_2H$), and 2-thiophenoxy acetic acid ($C_6H_5SCH_2COOH$).

Examples of chemical compounds of the structure phenyl-$R_9$—$R_{10}$ include acids, amines and amides of cinnamic acid ($C_6H_5CH=CHCOOH$), hydrocinnamic acid, dihydrocinnamic acid ($C_6H_5CH_2CH_2COOH$), a-methyl hydrocinnamic acid or dihydro cinnamic acid, 2,3-dimethyl hydrocinnamic or dihydrocinnamic acid, phenyl acetate ethyl ester ($C_6H_5CH(CH_3)CH_2COCH_2CH_3$), 2-phenoxypropionic acid ($C_6H_5OCH_2$ $CO_2H$), phenoxy acetic acid ($CH_3CH(OC_6H_5)$ $CO_2H$), and 3-phenyl butyric acid ($C_6H_5CH$ ($CH_3$) $CH_2COOH$). Additional chemical compounds which may or may not be included in the above classification scheme include monobutyrin, tributyrin ($CH_2(OCOCH_2CH_2CH_3)$ $CH(OCOCH_2CH_2CH_3)CH2(OCOCH_2CH_2CH_3)$, ethylphenyl acetic acid ($CH_3CH_2C_6H_5CH_2COOH$), indol-3-propionic acid, indol-3-butyric acid, 1- and 2-methyl cyclopropane carboxylic acid ($C_5H_8O_2$ and $C_6H_8O_2$), mercaptoacetic acid ($C_2H_4O_2S$), N-acetylglycine ($C_4H_7O_3N$), squaric acid ($C_4H_2O_4$), 4-trifluorobutanol ($C_4H_7OF_3$), chloropropionic acid ($ClCH_2CH_2CO_2H$), 3-trimethyl silyl-1-proposulfonic acid sodium ($C_6H_{15}O_3SS$), 2-oxopantansane ($C_5H_8O_3$), isobutyl hydroxylamine HCl ($C_4H_{12}OCl$), 2-methyl butanoic acid ($C_5H_{10}O_2$), o-benzoyl lactate, n-dimethylbutyric acid glycine amide, o-dimethyl butyric acid lactate, and diethyl butyric acid.

Agents are useful in pharmaceutical compositions for the treatment of cystic fibrosis. Preferred agents in such compositions include, for example, propionic acid, butyric acid, succinic acid, fumaric acid monoethyl ester, dimethyl butyric acid, trifluorobutanol ($C_4H_7OF_3$), chloropropionic acid ($ClCH_2CH_2COOH$), isopropionic acid, 2-oxypentasane ($CH_3CH_2CH_2C(O)COOH$), 2,2- or 3,3-dimethyl butyric acid ($C_6H_{12}O_2$), 2,2- or 3,3-diethyl butyric acid ($C_8H_{16}O_2$), butyric acid ethyl ester, 2-methyl butanoic acid ($C_5H_{10}O_2$), fumaric acid ($C_4H_4O_3$) and amides and salts thereof. Other examples include methoxy acetic acid ($H_3C(O)CH_2COOH$), dimethyl butyric acid, methoxy propionic acid, N-acetylglycine ($H_3CC(O)NCH_2COOH$), mercaptoacetic acid ($HSCH_2COOH$), 1- or 2-methyl cyclopropane carboxylic acid ($C_5H_8O_2$), squaric acid ($C_4H_2O_4$), 2- or 3-phenoxy propionic acid, methoxy butyric acid, phenoxy acetic acid, 4-chloro-2-phenoxy 2-propionic acid, 2- or 3-phenoxy butyric acid, phenyl acetic acid, phenyl propionic acid, 3-phenyl butyric acid, ethyl-phenyl acetic acid, 4-chloro-2-phenoxy-2-propionic acid, n-dimethyl butyric acid glycine amide, o-benzoyl lactic acid, o-dimethyl butyric acid lactate, cinnamic acid, dihydrocinnamic acid ($C_6H_5CHCH_3$ COOH), a-methyl-dihydrocinnamic acid, thiophenoxy acetic acid, and amines, amides and salts of these chemicals.

Useful amines and amides include isobutylhydroxylamine:HCl ($C_4H_{12}OCl$), fumaric acid monoamide ($C_4H_5O_2N$), fumaramide ($H_2NCOCHCHCONH_2$), succinamide and isobutyramide ($C_4H_9ON$). Salts can be sodium, potassium, calcium, ammonium, lithium or choline such as sodium 3-trimethyl silyl-1-proposulfonic acid ($C_6H_{15}O_3SiS:Na$). Reagents which may be electrostatically or covalently bonded with the inducing agent include amino acids such as arginine (arginine butyrate), glycine, alanine, asparagine, glutamine, histidine or lysine, nucleic acids including nucleosides or nucleotides, or substituents such as carbohydrates, saccharides, lipids, fatty acids, proteins or protein fragments. Combinations of these salts with the inducing agent can also produce useful new compounds from the interaction of the combination.

Chemical compounds are preferably optically pure with a specific conformation (plus {+} or minus {−}), absolute configuration (R or S), or relative configuration (D or L). Particular salts such as sodium, potassium, magnesium, calcium, choline, amino acid, ammonium or lithium, or combinations of salts may also be preferred, however, certain salts may be more advantageous than others. For example, chemical compositions that require high doses may introduce too much of a single salt to the patient. Sodium is generally an undesirable salt because at high doses, sodium can increase fluid retention resulting in tissue destruction. In such instances, lower doses or combinations of different or alternative salts can be used. For example, compounds of the invention may be substituted with one or more halogens such as chlorine (Cl), fluorine (F), iodine (I), bromine (Br) or combinations of these halogens. As known to those of ordinary skill in the art, halogenation can increase the polarity, hydrophilicity or lipophilicity or a chemical compound which can be a desirable feature, for example, to transform a chemical compound into a composition which is more easily tolerated by the patient or more readily absorbed by the epithelial lining of the gastrointestinal tract. Such compositions could be orally administered to patients.

Therapeutically effective chemical compounds may be created by modifying any of the above chemical compounds so that after introduction into the patient, these compounds metabolize into active forms, such as the forms above, which have the desired effect on the patient. Compounds may also be created which are metabolized in a timed-release fashion allowing for a minimal number of introductions which are efficacious for longer periods of time. Combinations of chemical compounds can also produce useful new compounds from the interaction of the combination. Such compounds may also produce a synergistic effect when used in combination with other known or other compounds.

Compositions are preferably physiologically stable at therapeutically effective concentrations. Physiological stable compounds are compounds that do not break down or otherwise become ineffective upon introduction to a patient prior to having a desired effect. Compounds are structurally resistant to catabolism, and thus, physiologically stable, or coupled by electrostatic or covalent bonds to specific reagents to increase physiological stability. Such reagents include ammo acids such as arginine, glycine, alanine, asparagine, glutamine, histidine or lysine, nucleic acids including nucleosides or nucleotides, or substituents such as carbohydrates, saccharides and polysaccharides, lipids, fatty acids, proteins, or protein fragments. Useful coupling partners include, for example, glycol such as polyethylene glycol, glucose, glycerol, glycerin and other related substances.

Physiological stability can be measured from a number of parameters such as the half-life of the compound or the half-life of active metabolic products derived from the compound. Certain compounds of the invention have in vivo half lives of greater than about fifteen minutes, preferably greater than about one hour, more preferably greater than about two hours, and even more preferably greater than about four hours, eight hours, twelve hours or longer. Although a compound is stable using this criteria, physiological stability cam also be measured by observing the duration of biological effects on the patient. Clinical symptoms which are important from the patient's perspective include a reduced frequency or duration, or elimination of the need for oxygen, inhaled medicines, or pulmonary therapy. Preferably, a stable compound of the invention has an in vivo half-life of greater than about 15 minutes, a serum half-life of greater than about 15 minutes, or a biological effect which continues for greater than 15 minutes after treatment has been terminated or the serum level of the compound has decreased by more than half.

Preferably, compositions are also not significantly biotransformed, degraded or excreted by catabolic processes associated with metabolism. Although there may be some biotransformation, degradation or excretion, these functions are not significant if the composition is able to exert its desired effect.

Compositions are also preferably safe at effective dosages. Safe compositions are compositions that are not substantially toxic (e.g. cytotoxic or myelotoxic), or mutagenic at required dosages, do not cause adverse reactions or side effects, and are well-tolerated. Although side effects may occur, compositions are substantially safe if the benefits achieved from their use outweigh disadvantages that may be attributable to side effects. Unwanted side effects include nausea, vomiting, hepatic or renal damage or failure, hypersensitivity, allergic reactions, cardiovascular problems, gastrointestinal disturbances, seizures and other central nervous system difficulties, fever, bleeding or hemorrhaging, serum abnormalities and respiratory difficulties.

Compositions useful for treating disorders preferably do not substantially affect the viability of a cell such as a normal mammalian cell, the cell being treated or effected by the chemical compound. Normal cell viability, the viability of an untransformed or uninfected cell, can be determined from analyzing the effects of the composition on one or more biological processes of the cell. Detrimental interference with one or more of these cellular processes becomes significant when the process becomes abnormal. Examples of quantitatable and qualifiable biological processes include the processes of cell division, protein synthesis, nucleic acid (DNA or RNA) synthesis, nucleic acid (principally DNA) fragmentation and apoptosis. Others processes include specific enzyme activities, the activities of the cellular transportation systems such as the transportation of amino acids by system A (neutral), system B (acidic) or system C (basic), and the expression of a cell surface protein. Each of these parameters is easily determined as significantly detrimental, for example, in tissue culture experiments, in animal experiments or in clinical studies using techniques known to those of ordinary skill in the art. Abnormal cell division, for example, can be mitosis which occurs too rapidly, as in a malignancy, or unstably, resulting in programmed cell death or apoptosis, detected by increased DNA degradation. The determination of abnormal cell viability can be made on comparison with untreated control cells. Compositions preferably increase normal cell viability. Increased cell viability can be determined by those of ordinary skill in the art using, for example, DNA fragmentation analysis. A decreased amount of fragmentation indicates that cellular viability is boosted. Determinations of increased or decreased viability can also be concluded from an analysis of the results of multiple different assays. Where multiple tests provide conflicting results, accurate conclusions can still be drawn by those of ordinary skill based upon the cell type, the correctness or correlation of the tests with actual conditions and the type of composition.

Compositions can be prepared in solution as a dispersion, mixture, liquid, spray, capsule or as a dry solid such as a powder or pill, as appropriate or desired. Solid forms may be processed into tablets or capsules or mixed or dissolved with a liquid such as water, alcohol, saline or other salt solutions, glycerol, saccharides or polysaccharide, oil or a relatively inert solid or liquid. Liquids, pills, capsules or tablets administered orally may also include flavoring agents to increase palatability. Additionally, all compositions may further comprise agents to increase shelf-life, such as preservatives, anti-oxidants and other components necessary and suitable for manufacture and distribution of the composition. Compositions further comprise a pharmaceutically acceptable carrier. Carriers are chemical or multi-chemical compounds that do not significantly alter or effect the active ingredients of the compositions. Examples include water, alcohols such as glycerol and polyethylene glycol, glycerin, oils, salts such as sodium, potassium, magnesium and ammonium, fatty acids, saccharides or polysaccharides. Carriers may be single substances or chemical or physical combinations of these substances.

Another embodiment of the invention is directed to combinations of compositions comprising a chemical compound in combination with an agent known to positively affect expression of the CFTR molecule. The agent may be a chemical compound such as glycerol, acetic acid, butyric acid, D- or L-amino-n-butyric acid, alpha- or beta-amino-n-butyric acid, arginine butyrate or isobutyramide, all disclosed in U.S. Pat. Nos. 4,822,821 and 5,025,029. Others include butyrin, 4-phenyl butyrate ($C_6H_5CH_2CH_2CH_2COOH$), phenylacetate ($C_6H_5CH_2COOH$), phenoxy acetic acid, all of which and more are disclosed in U.S. Pat. No. 4,704,402, and U.S. patent application Ser. No. 08/398,588 (entitled "Compositions for the Treatment of Blood Disorders" filed Mar. 3, 1995), and derivatives, salts and combination of these agents. The agent may be a protein such as hsp70 or a growth factor or cytokine. The agent may be a gene or a nucleotide sequence. Such composition may have additive or synergistic effects.

In another embodiment, compositions of the invention may contain one or more chemical compounds that increase the extent or magnitude of CFTR function, increase the expression of the CFTR molecule, increase transport of the CFTR molecule to the cell surface, increase the half-life (physical stability or thermal stability) of the chloride secretion in a $\Delta F508$-homozygous pancreatic acinar cell line (Cheng et al.). The results observed were consistent with 4PBA increasing the amount of $\Delta F508$-CFTR protein produced, but their data demonstrated that this was not due to a transcriptional regulatory effect of 4PBA on the CFTR gene. In immunoblot experiments, increased CFTR immunoreactivity was observed in the 4PBA-treated samples. Increased CFTR immunoreactivity was also observed by immunocytochemistry after 4PBA treatment, but no changes in CFTF RNA levels were found with 4PBA treatment. The authors further stated that butyrate and 4PBA have effects in IB3-1 cells that are qualitatively different from one another. Respiratory epithelial cells treated with 1-2 mM 4PBA are healthy, grow at a similar rate and with a similar morphology to control cells, and express CFTR channel activity at the plasma membrane. Equimolar concentrations of butyrate caused morphologic changes in IB3-1 cells, with rounding of cells and decreased growth rate.

This seems to indicate that 4PBA and butyrate may have different toxicity profiles and dose-response relationships. In addition, other published observations with butyrate in ΔF508-CFTR transfected C-127 cells found that the ~180-kD mature glycosylated species of CFTR was not observed after 5 mM butyrate treatment for 24 hours, despite a massive increase in ΔF508-CFTR mRNA as demonstrated by Northern analysis (Cheng et al.). This data thus did not demonstrate any effects of butyrate on CFTR protein levels or function, only changes in cellular morphology and cell death (Rubenstein et al.). Rubenstein et al observed no increases in CFTR mRNA in response to 4PBA and indicated that the mechanism of action of 4PBA was not similar to that of butyrate or related to increasing ΔF508-CFTR transcription. In addition, no increases in cAMP-stimulation was observed which would be indicative of chloride ion transport even after treatment with up to 300 mM butyrate (Cheng et al.).

These data argue against any beneficial or therapeutic effect of butyrate on cystic fibrosis. In fact, some authors even stated that butyrate is likely too toxic to use clinically (Rubenstein et al.). Further, the authors made a strong case that 4PBA, which molecule, increase expression from the CFTR gene, increase CFTR transcript levels, or increase post-transcriptional processes which increase the levels of CFTR transcript, or increase translation or enhance post-translational processing of the CFTR gene product. Stimulation of specific gene expression involves activation of transcription or translation promoters or enhancers, or alteration of the methylation patterns or histone distribution along the gene to promote expression. Expression may also be stimulated by inhibition of specific transcriptional or translational repressors, activation of specific transcriptional or translational activation factors, or activation of receptors on the surface of particular populations of cells. Stimulation may recruit additional epithelial cells to the airways, reprogram differentiated epithelial cells to express CFTR. Stimulation may also activate a previously dormant or relatively inactive gene.

Compositions of the invention may be administered by oral, parenteral, sublingual, rectal or enteral administration, or pulmonary absorption or topical application. Compositions cam be directly or indirectly administered to the patient. Indirect administration is performed, for example, by administering the composition to cells ex vivo and subsequently introducing the treated cells to the patient. The cells may be obtained from the patient to be treated or from a genetically related or unrelated patient. Related patients offer some advantage by lowering the immunogenic response to the cells to be introduced. For example, using techniques of antigen matching, immunologically compatible donors can be identified and utilized.

Direct administration of a composition may be by oral, parenteral, sublingual, rectal such as suppository or enteral administration, or by pulmonary absorption or topical application. Parenteral administration may be by intravenous injection, subcutaneous injection, intramuscular injection, intra-arterial injection, intrathecal injection, intraperitoneal injection or direct injection or other administration to the desired site. Injectable forms of administration are sometimes preferred for maximal effect. When long term administration by injection is necessary medi-ports, in-dwelling catheters, or automatic pumping mechanisms are also preferred wherein direct and immediate access is provided to the arteries in and around the heart and other major organs and organ systems.

An effective method of administration to a specific site may be by transdermal transfusion such as with a transdermal patch, by direct contact to the cells or tissue, if accessible, such as a skin tumor, or by administration to an internal site through an incisions or some other artificial opening into the body. Compositions may also be administered to the nasal passages as a spray. Diseases localized to the head and brain area are treatable in this fashion as arteries of the nasal area provide a rapid and efficient access to the upper areas of the head. Sprays also provide immediate access to the pulmonary system and are the preferable methods for administering compositions to these areas. Access to the gastrointestinal tract is gained using oral, enema, or injectable forms of administration. Compositions may be administered as a bolus injection or spray, or administered sequentially over time (episodically) such as every two, four, six or eight hours, every day (QD) or every other day (QOD), or over longer periods of time such as weeks to months.

Orally active compositions are preferred, as oral administration is usually the safest, most convenient and economical mode of drug delivery. Oral administration is usually disadvantageous because compositions are poorly absorbed through the gastrointestinal lining. Compounds which are poorly absorbed tend to be highly polar. Consequently, compounds which are effective, as described herein, may be made orally bioavailable by reducing or eliminating their polarity. This can often be accomplished by formulating a composition with a complimentary reagent which neutralizes its polarity, or modifying the compound with a neutralizing chemical group. Oral bioavailability is also a problem because drugs are exposed to the extremes of gastric pH and gastric enzymes. These problems can be overcome in a similar matter by modifying the molecular structure to be able to withstand very low pH conditions and resist the enzymes of the gastric mucosa such as by neutralizing an ionic group, by covalently bonding an ionic interaction, or by stabilizing or removing a disulfide bond or other relatively labile bond.

Compounds may also be used in combination with other agents to maximize the effect of the compositions in an additive or synergistic manner. Cytokines which may be effective in combination with the compositions of the invention include growth factors such as B cell growth factor (BCGF), fibroblast-derived growth factor (FGF), granulocyte/macrophage colony stimulating factor (GM-CSF), granulocyte colony stimulating factor (G-CSF), macrophage colony stimulating factor (M-CSF), epidermal growth factor (EGF), vascular endothelial growth factor (VEGF), platelet derived growth factor (PDGF) nerve growth factor (NGF), stem cell factor (SCF), and transforming growth factor (TGF). These growth factors plus a composition may further stimulate cellular differentiation and/or the expression of the CFTR molecule or function.

Alternatively, other cytokines and related antigens in combination with a composition may also be useful to treat cystic fibrosis. Potentially useful cytokines include tumor necrosis factor (TNF), the interleukins IL-I, IL-2, IL-3, IL-4, IL-5, IL-6, etc., recombinant IL receptors, growth factors, colony stimulating factors, erythropoietin (EPO), the interferon (IFN) proteins IFN-alpha, IFN-beta, and IFN-gamma; cyclic AMP including dibutyryl cyclic AMP, hemin, DMSO, hydroxyurea, hypoxanthine, glucocorticoid hormones and cytosine arabinoside. Therapies using combinations of these agents would be safe and effective therapies cystic fibrosis. Combinations of therapies may also be effective in inducing improvement of the symptoms of cystic fibrosis such as compositions of the invention plus the reintroduction of a normal or altered CFTR gene (gene therapy), toxin or drug conjugated antibody therapy using monoclonal or polyclonal antibodies directed against the pulmonary cells, or specific anti-sense therapy. Effects may be additive, logarithmic or synergistic, and methods involving combinations of therapies may be simultaneous protocols, intermittent protocols or protocols which are empirically determined.

Another embodiment of the invention is directed to the pulsed administration of pharmaceutical compositions for the treatment or prevention of cystic fibrosis. Pulsed administration is surprisingly more effective than continuous treatment as pulsed doses are often lower than would be expected from continuous administration of the same composition. Each pulse dose can be reduced and the total amount of drug administered over the course of treatment to the patient is minimized.

In traditional forms of therapy, repeated administration is designed to maintain a desired level of an active ingredient in the body. Very often, complications that develop can be attributed to dosage levels that, to be effective, are near toxic or otherwise harmful to normal cells. In contrast, with pulse therapy, in vivo levels of drug drop below that level required for effective continuous treatment. Therefore, pulsing is not simply the administration of a sufficiently large bolus such that there will be therapeutically sufficient drug available for a long period of time. Pulsed administration can substantially reduce the amount of the composition administered to the patient per dose or per total treatment regimen with an increased effectiveness. This represents a significant saving in time, effort and expense and, more importantly, a lower effective dose substantially lessens the number and severity of complications that may be experienced by the patients. As such, pulsing is surprisingly more effective than continuous administration of the same composition.

Preferably, compositions contain chemicals that are substantially nontoxic. Substantially non-toxic means that the composition, although possibly possessing some degree of toxicity, is not harmful to the long-term health of the patient. Although the active component of the composition may not be toxic at required levels, there may also be problems associated with administering the necessary volume or amount of the final form of the composition to the patient. For example, if the composition contains a salt, although the active ingredient may be at a concentration that is safe and effective, there can be a harmful build-up of sodium, potassium or another ion. With a reduced requirement for the composition or at least the active component of that composition, the likelihood of such problems can be reduced or even eliminated. Consequently, although patients may have minor or short term detrimental side-effects, the advantages of taking the composition outweigh the negative consequences.

Compositions most effective at pulsed administration are typically nontoxic or non-cytotoxic chemicals without any substantial proteinaceous active component at the therapeutically effective pulsed dose. Preferably, treatment does not stimulate apoptosis in the cells being directly treated or in the otherwise normal cells of the body which will also be exposed to the composition.

Individual pulses can be delivered to the patient continuously over a period of several hours, such as about 2, 4, 6, 8, 10, 12, 14 or 16 hours, or several days, such as 2, 3, 4, 5, 6, or 7 days, preferably from about 1 hour to about 24 hours and more preferably from about 3 hours to about 9 hours. Alternatively, periodic doses can be administered in a single bolus or a small number of injections of the composition over a short period of time, typically less than 1 or 2 hours. For example, arginine butyrate has been administered over a period of 4 days with infusions for about 8 hours per day or overnight, followed by a period of 7 days of no treatment. The interval between pulses or the interval of no delivery is greater than 24 hours and preferably greater than 48 hours, and can be for even longer such as for 3, 4, 5, 6, 7, 8, 9 or 10 days, two, three or four weeks or even longer. As the results achieved may be surprising, the interval between pulses, when necessary, can be determined by one of ordinary skill in the art. Often, the interval between pulses can be calculated by administering another dose of the composition when the composition or the active component of the composition is no longer detectable in the patient prior to delivery of the next pulse. Intervals can also be calculated from the in vivo half-life of the composition. Intervals may be calculated as greater than the in vivo half-life, or 2, 3, 4, 5 and even 10 times greater the composition half-life. For compositions with fairly rapid half lives such as arginine butyrate with a half-life of 15 minutes, intervals may be 25, 50, 100, 150, 200, 250 300 and even 500 times the half life of the chemical composition.

The number of pulses in a single therapeutic regimen may be as little as two, but is typically from about 5 to 10, 10 to 20, 15 to 30 or more. In fact, patients can receive drugs for life according to the methods of this invention without the problems and inconveniences associated with current therapies. Compositions can be administered by most any means, but are preferably delivered to the patient as an injection (e.g. intravenous, subcutaneous, intraarterial), infusion or instillation, and more preferably by oral ingestion. Various methods and apparatus for pulsing compositions by infusion or other forms of delivery to the patient are disclosed in U.S. Pat. Nos. 4,747,825; 4,723,958; 4,948,592; 4,965,251 and 5,403,590.

Compositions administered in pulses have the surprising benefit of reducing the overall load of drug on the patient as the total amount of drug administered can be substantially less than that amount that has been therapeutically administered by conventional continuous therapy. Substantially means that there is more than an insignificant difference between the amount or concentration of a composition administered by pulsing according to the invention verses the amount or concentration administered using conventional therapy, without compromising the beneficial effect achieved to the patient. For example, arginine butyrate has been shown to be effective at continuous administration at about 2000 mg/kg patient weight. Doses of between about 400 to 1500 mg/kg, preferably from about 600 to 1000 mg/kg and more preferably from 700 to 800 mg/kg, when administered in pulses, are surprisingly more beneficial as measured by a rise in fetal hemoglobin levels in thalassemic patients. Typical pulsed amounts of arginine butyrate are from about 2 to about 20 g/kg/month, and preferably from about 3 to about 10 g/kg/month wherein the patient receives a total of less than about 20 kg per month, preferably less than about 15 kg per month and more preferably less than about 10 kg per month. The amounts administered per pulse as well as the total amount of the composition received by the patient over the regimen is substantially reduced. Preferably, the therapeutically effective pulsed dose is less than the continuous dose, or less than one half, one third, one quarter, one fifth, one tenth or even one twentieth of the therapeutic continuous dose of the same composition or even less.

Other embodiments and uses of the invention will be apparent to those skilled in the art from consideration of the specification and practice of the invention disclosed herein. All U.S. patents and patent applications, including provisional applications, and all other documents referenced herein, for whatever reason, are specifically incorporated by reference. It is intended that the specification and examples be considered exemplary only, with the true scope and spirit of the invention being indicated by the following claims.

We claim:

1. A method for the treatment of cystic fibrosis comprising the administration to a patient of a composition comprising a physiologically-effective amount of 2,2-dimethyl butyric acid, or a salt thereof.

2. The method of claim 1 wherein administration is pulsed administration or timed-release administration.

3. The method of claim 2 wherein the pulsed administration comprises a plurality of individual pulses delivered to the patient continuously over a period of 2 hours, 4 hours, 6 hours, 8 hours, 10 hours, 12 hours, 14 hours, 16 hours, 2 days, 3 days, 4, days, 5 days, 6 days, 7 days, two weeks, three weeks or four weeks.

4. The method of claim 2 wherein the pulsed administration comprises a plurality of individual pulses delivered at regular intervals measuring from between 3 to 9 hours.

5. The method of claim 1 wherein the composition further comprises a pharmaceutically acceptable carrier.

6. The method of claim 1 where in the composition further comprises a compound that increases expression of a CFTR molecule as compared to the level of expression in the absence of administration of the ageat compound.

7. The method of claim 6, wherein the compound that increases expression of the CFTR molecule as compared to the level of expression in the absence of administration of the compound, increases the extent or magnitude of CFTR function, increases the expression of the CFTR molecule, increases transport of the CFTR molecule to the cell surface, increases half-life of the CFTR molecule, increases expression from a CFTR gene, increases CFTR transcript levels, increases post-transcriptional processes which increase CFTR transcript levels in the cell, or increases translation post-translational processing of a CFTR gene product.

8. The method of claim 1 wherein the composition further treats defective chloride ion transport.

9. A method for the therapy of cystic fibrosis comprising administering to a patient a quantity of an agent, or pharmaceutically acceptable salt thereof, effective for said therapy, said agent being 2,2-dimethyl butyric acid, or a salt thereof.

10. A method for increasing expression of CFTR as compared to the level of expression in the absence of administration of an agent comprising the administration of a physiological effective amount of said agent which is 2,2-dimethyl butyric acid, or a pharmaceutically acceptable salt thereof.

11. The method of claim 10 wherein administration is pulsed administration.

12. The method of claim 10 wherein enhancement of the expression of CFTR comprises increasing the expression of CFTR genes, increasing the number of CFTR-expressing cells or increasing the function or activity of CFTR as compared to the level of expression number of CFTR-expressing cells or the function or activity that is present in the absence of administration of the agent.

13. The method of claim 10 wherein CFTR expression is increased greater than about 30% as compared to the level of expressionin the absence of administration of the agent.

14. The method of claim 10 wherein CFTR expression is increased greater than about 100% as compared to the level of expression in the absence of administration of the agent.

15. The method of claim 10 wherein CFTR expression is increased greater than about 20% as compared to the level of expression in the absence of administration of the agent.

16. The method of claim 1, wherein the composition administered is a salt thereof and is sodium 2-2-dimethyl-butyric acid.

17. The method of claim 12, wherein the composition administered is a salt thereof and is sodium 2-2-dimethyl-butyric acid.

* * * * *